United States Patent [19]

Watson et al.

[11] Patent Number: 4,915,724
[45] Date of Patent: Apr. 10, 1990

[54] FUNGAL HERBICIDE FOR CONTROL OF LAMB'S QUARTERS AND OTHER CHENOPODIUM WEEDS

[75] Inventors: Alan Watson, Pincourt; William Allan; Lee Wymore, both of Ste-Anne de Bellevue, all of Canada

[73] Assignee: The Royal Institution for the Advancement of Learning, Montreal, Canada

[21] Appl. No.: 201,211

[22] Filed: Jun. 2, 1988

[30] Foreign Application Priority Data

Jun. 16, 1987 [CA] Canada ................................. 539789

[51] Int. Cl.$^4$ ...................... D01N 0/00; C12R 1/645
[52] U.S. Cl. .......................................... 71/65; 71/79; 435/911
[58] Field of Search ...................... 71/79, 65; 435/911

[56] References Cited

U.S. PATENT DOCUMENTS 4,775,405 10/1988 Caulder et al. ......................... 71/79
4,776,873 10/1988 Caulder et al. ......................... 71/79

Primary Examiner—Richard L. Raymond
Assistant Examiner—Raymond Covington
Attorney, Agent, or Firm—Cushman, Darby & Cushman

[57] ABSTRACT

A method for controlling growth of plants of Chenopodium weed species in agricultural crops. This method comprises applying to the plants or to the locus of the plants an effective amount of the fungus *Ascochyta hyalospora* to effect and produce typical lesions so as to inhibit the growth of or kill the plants.

12 Cla

FUNGAL HERBICIDE FOR CONTROL OF LAMB'S QUARTERS AND OTHER CHENOPODIUM WEEDS

This invention relates to a method for the biological control of weeds and, more particularly, to such a method using a fungal pathogen.

Lamb's-quarters (*Chenopodium album* L.) is an annual weedy plant with a wide distribution throughout the world. It can be found growing from lat 70° N to lat 50° S and is one of the five most widely distributed plants in the world. The plant is a very successful colonizer of disturbed soil and is a serious weed problem in cultivated crops such as sugar beets, corn, soybeans, and cereal crops.

The morphological features of the plant are quite variable. The plant is an erect annual herb that grows up to 2.5 meters in height. The ridged, branching stems often have reddish parallel stripes arranged length-wise. The simple, alternate leaves have shapes that range from ovate-lanceolate to rhombic-lanceolate. Although there are no distinct lobes, the leaves can have up to 10 shallow lobes. The leaf surface is glabrous with a mealy, farinose texture. No stipules are present. The inflorescence, a spike pannicle, has green perfect flowers with 5 sepals and no petals. The plants are wind-pollinated, with large plants producing up to 500,000 seeds.

Because of its plentiful seed production and prevalence, lamb's-quarters forms a large proportion of the residual seedbank in the soil. The plant has no special method of dispersal other than shedding of seeds around the parent plant. Therefore, lamb's-quarters is normally found in patches that are often dense and uniform. If not controlled, the weed can very quickly become troublesome and competitive in the crop. Apart from the competition that it offers the crop, the weed can be poisonous to some livestock if large quantities are consumed. The seed is also found as impurities in crop seeds and the pollen can cause allergies.

Normally, lamb's-quarters is easily controlled through cultural and chemical methods. For example, preplant incorporated, pre-emergence, and post-emergence applications of atrazine provide excellent control of lamb's-quarters in corn. Shallow mechanical cultivations are also used to assist in the control of small seedlings. However, there are problems with some of the control methods. Apart from the general concern with chemical pesticide contamination of the environment, there are more specific concerns with triazine resistant lamb's-quarters plants. These resistant plants have become a problem in North America and western Europe. In western Europe triazine resistance has also been reported in the related species, *C. polyspermum* and *C. ficifolium*. When this resistance appears, other control measures are necessary such as alternative herbicides, greater use of crop rotation, and mechanical cultivation. However, these other control measures are not always possible or desirable. With the increased use of minimum tillage techniques, less reliance is placed on mechanical cultivation and crop rotation is not as easy to use. Therefore, greater use of chemical herbicides is often necessary for weed control.

Although the merits of using plant pathogens to control weeds in annual crops have been discussed previously for Colletotrichum species (U.S. Pat. No. 3,849,104 and No. 3,999,973), Fusarium species (U.S. Pat. No. 4,419,120), and Alternaria species (U.S. Pat. No. 4,390,360), no plant pathogens have been used to date to control the problem of lamb's-quarters and triazine resistant lamb's-quarters.

It is the object of this invention to provide a biological control method for lamb's-quarters in agricultural crops. The pathogen can also be used to control other Chenopodium weed species that are susceptible to the pathogen. The pathogen can also be used in combination with chemical herbicides and/or other pathogens to enhance the control of lamb's-quarters and/or other weeds.

The fungal pathogen, *Ascochyta hyalospora*, described in this invention, was discovered on the research station of Macdonald College in Ste-Anne-de-Bellevue, Quebec in September, 1985. The original isolate was obtained from diseased leaf tissue and labelled ChA 02A. The isolation technique was a commonly used method in which pieces of diseased leaf tissue are immersed in 70% ethanol for 30 seconds, transferred to 2% sodium hypochlorite for approximately 60 seconds, and rinsed twice with sterile distilled water. After drying on filter paper, the leaf pieces are placed on Potato Dextrose Agar (PDA) medium. For storage, the isolated strain was grown on PDA in a glass storage vial. When the desired amount of growth was obtained, mineral oil was added and the storage vials were placed in a refrigerator. Four other strains—ChA 02H, ChA 02W, ChA 02EE, and ChA 02FF—were used in the studies along with ChA 02A. The strain, ChA 02H, is a combination of three single conidia isolates of ChA 02A. ChA 02W was a mycelial transfer from the advancing edge of an Ascochyta colony growing from a piece of leaf tissue infected with the ChA 02A strain. ChA 02FF and ChA 02EE are single conidial strains isolated from ChA 02W. All strains are subcultures of the original isolate, ChA 02A.

When used in laboratory tests, the pathogen was found to damage or kill lamb's-quarters without harming common agricultural crop plants. The fungus has been shown in the tests to be capable of heavily defoliating a lamb's-quarters plant of any age as well as infecting the stems of young seedlings. Foliar infection with the appropriate amount of inoculum results in coalescing lesions on the leaf with the ultimate abscission of that leaf. Stem infection of a young seedling, under suitable conditions, results in death of the plant.

Growth on culture media and measurements of conidial and pycnidial characteristics of our isolate are similar to the descriptions provided by Boerema et al (1977) and van der Aa & van Kesteren (1979). Colonies of ChA 02W and ChA 02FF attained a diameter of 39–40 mm on oatmeal agar after 8 days at 27C. Colonies of the same fungal strains attained diameters of 27–29 mm on malt extract agar. On oatmeal agar, the fungus appeared as a dark mat of appressed mycelium with dark pycnidia scattered about the central portion of the colony. The upper side of the colony had an olivaceous colour while the reverse side was greenish-glaucus to olivaceous in colour. On inoculated lamb's-quarters stems the pycnidia attained a diameter of approximately 200–275 $\mu$m. The conidia were usually 20–25 $\mu$m $\times$ 7.5–10 $\mu$m. The pycnidia on inoculated leaves commonly ranged from 175–230 $\mu$m in diameter.

*Ascochyta hyalospora* (Cooke & Ellis) Boerema et al. is on deposit with the Department of Plant Science, Macdonald College of McGill University in Ste. Anne-de-Bellevue, Quebec. It is also deposited at the Commonwealth Mycological Institute in Kew, England, and has been assigned the accession number IMI 302770.

EXAMPLE I

This example illustrates the production and preparation of inoculum for spraying onto lamb's-quarters.

Regardless of the strain that was used, production and preparation of inoculum was similar for each experiment. The strains were stored in a refrigerator as oil-covered vials. For each experiment, starter or seed cultures were begun by placing a small piece of mycelium from the storage culture onto the centre of a petri plate. The medium used for the starter culture was either Torula Yeast Agar [15 g/L torula yeast, 1 g/L $K_2HPO_4$, 0.5 g/L $MgSO_4.7H_2O$, 20 g/L agar, and 100 mg/L novobiocin] or a mixture of ½ strength Torula Yeast Agar and ½ strength Potato Dextrose Agar [19.5 g/L potato dextrose agar, 7.5 g/L torula yeast, 0.5 g/L $K_2HPO_4$, 0.25 g/L $MgSO_4.7H_2O$, 10 g/L agar, and 100 mg/L]. One to three week old seed cultures were used to begin production plates. A needle was used to transfer a mixture of pycnidia and conidia from the seed culture to the production plate. To facilitate better coverage of the plate, separate colonies were begun at three locations on the plate. The production plates were harvested after two to three weeks of growth in a cabinet set for 12 hours of darkness followed by 12 hours of fluorescent and near-U.V. light. Temperature was 24C. during the light period and 22C. during the dark period. The following procedure was developed for harvesting the conidia:

(1) Plate were scraped using a spatula. The scraped pycnidia and mycelium were placed in a beaker of water. After all plates had been scraped, the beaker containing the scraped material was placed on a magnetic stirrer for 15 to 30 minutes.

(2) The stirred material was strained through several layers of cheesecloth. When a large amount of material was harvested, a 250 m metal sieve was also used along with the cheesecloth.

(3) The filtered conidia were centrifuged once at 5000 rpm, resususpended in distilled water and centrifuged a second time at 3000 rpm.

(4) Water was added to adjust the suspension to the required concentration for the experiment.

When the above methods were used, conidia production ranged from $3.7\times10^6$ to $1.2\times10^7$ conidia/plate.

Another method for conidia production, using soybeans in 250-ml flasks, was also devised. Soybeans were boiled for approximately 15 minutes to soften and moisten the seeds. One hundred bean seeds were placed in each 250-ml flask. The flasks were autoclaved for 20 minutes and then allowed to cool to room temperature. Three days later, the flasks were autoclaved once more. When the flasks were cool, 3 ml of a dilute suspension of *Ascochyta conidia* were pipetted into the flask. The fungus grew in the flasks which were kept on a laboratory bench at room temperature. After 6 days, mycelium had grown over the surface of the seeds, and pycnidial initials were visible. At this time, the flasks were transferred to a near U.V. light chamber (constant near U.V., 27C.). Yields of up to $4\times10^7$ conidia/flask were obtained when flasks were harvested after 11 days.

EXAMPLE II

This example illustrates the effect of plant age and inoculum concentration on disease development.

The results of two separate experiments are shown in the accompanying tables. In the first experiment (Tables 1, 2 and 3), transplants of age 3 days, 13 days, and 23 days were sprayed at rates of $1\times10^5$ conidia/m$^2$, $1\times10^6$/m$^2$, $1\times10^7$, $1\times10^8$/m$^2$, and no conidia/m$^2$. Each treatment consisted of a 7.5 cm pot containing 1 plant. Each treatment was replicated ten times. After spraying, the plants were subjected to a leaf wetness period of 20 hours at 22C. The plants were then placed in a growth cabinet set at 22C. day/16C. night with a 14-hour photoperiod. Height and dry matter production were measured 22 days after spraying.

TABLE 1

Effect of inoculum rates on 3-day old transplants (cotyledon stage)

| Inoculum (conidia/m$^2$) | Mortality[1] (%) | Height[2] (cm/pot) | Dry Matter[3] (g/pot) |
|---|---|---|---|
| 0 | 0 | 11.1 a[4] | 0.147 a |
| $1\times10^5$ | 0 | 8.8 a | 0.1071 a |
| $1\times10^6$ | 10 | 4.5 b | 0.049 b |
| $1\times10^7$ | 80 | 0.6 c | 0.007 bc |
| $1\times10^8$ | 100 | 0.0 c | 0 c |

[1]Percent mortality is based on the total number of dead plants per treatment. A total of 10 plants/treatment were tested. The data displayed in the mortality column was subjected to Probit Analysis. Under the conditions of this experiment, the estimated median lethal dose (LD50) was $4.0\times10^6$ conidia/m$^2$. With a fiducial probability of 0.95, the true LD50 could lie between $1.6\times10^6$ conidia/m$^2$ and $9.8\times10^6$ conidia/m$^2$.
[2]The figures in this column are means of the vertical plant height which was measured from the soil surface to the apical meristem.
[3]The figures in this column are the dry weight means of the above-ground portion of the plants.
[4]Means followed by the same letter in a column are not significantly different at P = 0.05, according to Tukey's (HSD) Test.

TABLE 2

Effect of inoculum rates on 13-day old transplants (4–6 leaf stage)

| Inoculum (conidia/m$^2$) | Disease Rating[1] (%) | Mortality[2] (%) | Height[3] (cm/pot) | Dry Matter[4] (g/pot) |
|---|---|---|---|---|
| 0 | 0 | 0 | 27.0 | 0.542 a |
| $1\times10^5$ | 0.4 | 0 | 26.4 a | 0.587 a |
| $1\times10^6$ | 6.5 | 0 | 26.8 a | 0.567 a |
| $1\times10^7$ | 73.6 | 0 | 17.2 b | 0.356 a |
| $1\times10^8$ | 99.3 | 100 | 0.0 c | 0.006 c |

[1]Disease ratings, based on the Barratt-Horsfall rating scale, were conducted 8 days after spraying. The figures represent the average % area of the leaf affected by disease for each treatment. The four bottom leaves of each plant were rated.
[2]Percent mortality is based on the total number of dead plants per treatment. A total of 10 plants/treatment were tested.
[3]The figures in this column are the means of the vertical plant height which was measured from the soil surface to the apical meristem.
[4]The figures in this column are the dry weight means of the above-ground portion of the plants.
[5]Means followed by the same letter in a column are not significantly different at P = 0.05, according to Tukey's (HSD) Test.

TABLE 3

Effect of inoculum rates on 23-day old transplants (8–10 leaf stage)

| Inoculum (conidia/m$^2$) | Disease Rating[1] (%) | Mortality[2] (%) | Height[3] (cm/pot) | Dry Matter[4] (g/pot) |
|---|---|---|---|---|
| 0 | 0 | 0 | 55.5 a[5] | 1.128 a |
| $1\times10^5$ | 4.8 | 0 | 53.1 a | 1.081 a |
| $1\times10^6$ | 76.0 | 0 | 53.8 a | 1.107 a |
| $1\times10^7$ | 95.7 | 0 | 52.4 a | 0.972 a |
| $1\times10^8$ | 100 | 0 | 34.4 b | 0.486 b |

[1]Disease ratings, based on the Barratt-Horsfall rating scale, were conducted 8 days after spraying. The figures represent the average % area of the leaf affected by disease for each treatment. The four bottom leaves of each plant were rated.
[2]Percent mortality is based on the total number of dead plants per treatment. A total of 10 plants/treatment were tested.
[3]The figures in this column are the means of the veritcal plant height which was measured from the soil surface to the apical meristem.
[4]The figures in this column are the dry weight means of the above-ground portion of the plants.
[5]Means followed by the same letter in a column are not significantly different at P = 0.05, according to Tukey's (HSD) Test.

In the second experiment (Tables 4, 5 and 6), transplants of age 5 days, 10 days, and 15 days were sprayed at rates of $1.6 \times 10^7$ conidia/m$^2$, $3.1 \times 10^7$/m$^2$, $6.3 \times 10^7$/m$^2$, $1.3 \times 10^8$/m$^2$, $2.5 \times 10^8$/m$^2$, $1 \times 10^9$/m$^2$, and no conidia/m$^2$. Each treatment consisted of a 12.5 cm pot containing 5 plants. Each treatment was replicated six times. After spraying, the plants were subjected to leaf wetness period of 20 hours at 22C. The plants were then placed in a growth cabinet set at 22C. day/16C. night with a 14 hour photoperiod. Height and dry matter production were measured 14 days after spraying.

TABLE 4

Effect of inoculum rates on 5-day old transplants (early 2-leaf stage)

| Inoculum (conidia/m$^2$) | Mortality[1] (%) | Height[2] (cm/pot) | Dry Matter[3] (g/pot) |
|---|---|---|---|
| 0 | 0 | 56.8 a[4] | 0.985 a |
| $1.6 \times 10^7$ | 0 | 43.0 b | 0.647 ab |
| $3.1 \times 10^7$ | 0 | 35.0 b | 0.535 bc |
| $6.3 \times 10^7$ | 6.7 | 30.8 b | 0.419 bcd |
| $1.3 \times 10^8$ | 26.7 | 15.5 c | 0.218 cde |
| $2.5 \times 10^8$ | 76.7 | 6.8 cd | 0.069 de |
| $5.0 \times 10^8$ | 93.3 | 2.0 d | 0.015 e |
| $1.0 \times 10^9$ | 96.7 | 1.2 d | 0.014 e |

[1] Percent mortality is based on the total number of dead plants per treatment. A total of 30 plants/treatment were tested. The data displayed in the mortality column was subjected to Probit Analysis. Under the conditions of this experiment, the estimated median lethal dose (LD50) was $1.8 \times 10^8$ conidia/m$^2$.
[2] The figures in this column are the means of the total vertical height of the 5 plants in each pot. Vertical heights were measured from the soil surface to the apical meristem.
[3] The figures in this column are the means of the total dry weight per pot for the above-ground portion of the plants.
[4] Means followed by the same letter in a column are not significantly different at P = 0.05, according to Tukey's (HSD) Test.

TABLE 5

Effect of inoculum rates on 10-day old transplants (4–6 leaf stage)

| Inoculum (conidia/m$^2$) | Mortality[1] (%) | Height[2] (cm/pot) | Dry Matter[3] (g/pot) |
|---|---|---|---|
| 0 | 0 | 108.2 a[4] | 3.121 a |
| $1.6 \times 10^7$ | 0 | 89.5 ab | 2.357 ab |
| $3.1 \times 10^7$ | 0 | 87.2 ab | 2.093 bc |
| $6.3 \times 10^7$ | 0 | 85.0 b | 2.185 bc |
| $1.3 \times 10^8$ | 0 | 73.2 bc | 1.742 bc |
| $2.5 \times 10^8$ | 6.7 | 56.5 c | 1.408 cd |
| $5.0 \times 10^8$ | 26.7 | 27.7 d | 0.601 de |
| $1.0 \times 10^9$ | 66.7 | 7.0 d | 0.168 e |

[1] Percent mortality is based on the total number of dead plants per treatment. A total of 30 plants/treatment were tested. The data displayed in the mortality column was subjected to Probit Analysis. Under the conditions of this experiment, the estimated median lethal dose (LD50) was $7.5 \times 10^8$ conidia/m$^2$.
[2] The figures in this column are the means of the total vertical height of the 5 plants in each pot. Vertical heights were measured from the soil surface to the apical meristem.
[3] The figures in this column are the means of the total dry weight per pot for the above-ground portion of the plants.
[4] Means followed by the same letter in a column are not significantly different at P = 0.05, according to Tukey's (HSD) Test.

TABLE 6

Effect of inoculum rates on 15-day old transplants (6–8 leaf stage)

| Inoculum (conidia/m$^2$) | Mortality[1] (%) | Height[2] (cm/pot) | Dry Matter[3] (g/pot) |
|---|---|---|---|
| 0 | 0 | 135.3 ab[4] | 3.742 ab |
| $1.6 \times 10^7$ | 0 | 144.0 ab | 3.918 a |
| $3.1 \times 10^7$ | 0 | 151.2 a | 3.620 ab |
| $6.3 \times 10^7$ | 0 | 126.2 ab | 3.079 bc |
| $1.3 \times 10^8$ | 0 | 110.2 bc | 2.752 cd |
| $2.5 \times 10^8$ | 3.3 | 87.2 cd | 2.076 de |
| $5.0 \times 10^8$ | 3.3 | 81.0 cd | 1.653 e |

TABLE 6-continued

Effect of inoculum rates on 15-day old transplants (6–8 leaf stage)

| Inoculum (conidia/m$^2$) | Mortality[1] (%) | Height[2] (cm/pot) | Dry Matter[3] (g/pot) |
|---|---|---|---|
| $1.0 \times 10^9$ | 13.3 | 63.3 d | 1.426 e |

[1] Percent mortality is based on the total number of dead plants per treatment. A total of 30 plants/treatment were tested.
[2] The figures in this column are the means of the total vertical height of the 5 plants in each pot. Vertical heights were measured from the soil surface to the apical meristem.
[3] The figures in this column are the means of the total dry weight per pot for the above-ground portion of the plants.
[4] Means followed by the same letter in a column are not significantly different at P = 0.05, according to Tukey's (HSD) Test.

EXAMPLE III

This example illustrates the effect of leaf wetness duration and air temperature during the first 24 hours of the infection process on disease development.

Transplanted lamb's-quarters at the 4-leaf stage were sprayed at a rate of $1 \times 10^8$ conidia/m$^2$. After spraying, the plants were placed in one of four dark growth cabinets. The growth cabinet temperatures were set at 12C., 18C., 24C. and 30C. Leaf wetness was maintained by placing plants in moistened plastic bags for the duration of their leaf wetness periods of 0, 6, 12, 18 and 24 hours. Therefore, the experiment was a 5×4 factorial. Each treatment combination consisted of 5 transplants per pot, and was replicated four times. Twenty-four hours after spraying, the plants were transferred to a growth cabinet at 22C. day/16C. night with a 14-hour photoperiod. The percentage leaf area affected 16C. night with a 14-hour photoperiod. The percentage leaf was affected by disease was evaluated 8 days after spraying. Height and dry matter were measured 14 days after spraying. The means of each treatment combination, averaged over 4 replications, are presented in Tables 7, 8 and 9.

TABLE 7

Effect of leaf wetness period and temperature on disease ratings of lamb's-quarters inoculated with *Ascochyta hyalospora*

| Leaf Wetness Period (hrs) | Temperature (C.) | | | |
|---|---|---|---|---|
| | 12 | 18 | 24 | 30 |
| 0 | 01 | 0 | 0 | 0 |
| 6 | 0.5 | 16.5 | 33.4 | 5.9 |
| 12 | 9.0 | 47.8 | 61.1 | 40.1 |
| 18 | 34.9 | 68.8 | 71.6 | 38.3 |
| 24 | 41.9 | 54.7 | 69.6 | 65.0 |

[1] Figures represent the % leaf area by the pathogen. The 4 bottom leaves of each plant were rated using the Barratt-Horsfall rating system. Each figure in the table is an average of four blocks.

TABLE 8

Effect of leaf wetness period and temperature on height (cm) of lamb's-quarters inoculated with *Ascochyta hyalospora*

| Leaf Wetness Period (hrs) | Temperature (C.) | | | | Mean |
|---|---|---|---|---|---|
| | 12 | 18 | 24 | 30 | |
| 0 | 52 | 54 | 57 | 47 | 52.5 |
| 6 | 56 | 45 | 29 | 49 | 44.75 |
| 12 | 42 | 33 | 22 | 41 | 34.5 |
| 18 | 31 | 24 | 21 | 37 | 28.25 |
| 24 | 30 | 21 | 23 | 27 | 25.25 |

TABLE 9

Effect of leaf wetness period and temperature on dry weight (g/pot) of lamb's-quarters inoculated with *Ascochyta hyalospora*

| Leaf Wetness Period (hrs) | Temperature (C.) | | | | |
|---|---|---|---|---|---|
| | 12 | 18 | 24 | 30 | Mean |
| 0 | 1.43 | 1.27 | 1.50 | 1.19 | 1.35 |
| 6 | 1.47 | 1.25 | 0.74 | 1.20 | 1.17 |
| 12 | 1.11 | 0.78 | 0.54 | 0.99 | 0.85 |
| 18 | 0.80 | 0.64 | 0.55 | 0.93 | 0.73 |
| 24 | 0.79 | 0.63 | 0.65 | 0.81 | 0.72 |

Across all temperatures tested, there is a consistent decline in height and dry weight and an increase in disease as leaf wetness duration is increased from 0 to 24 hours. The most severe decrease in growth occurred at 24C. with 12 to 24 hours of leaf wetness.

EXAMPLE IV

This example illustrates the effect on triazine resistant and triazine susceptible lamb's-quarters plants when the Ascochyta pathogen is used in conjunction with atrazine.

A test was conducted using atrazine and Ascochyta (ChA 02W) in various combinations. Four treatment combinations were used: control (water only), Ascochyta (ChA 02W), atrazine (500 g/l), and Ascochyta+atrazine (tank mix). The Ascochyta was applied at a rate of $1 \times 10^8$ conidia/m$^2$, and the atrazine was applied at a rate of 2.24 kg/ha. Each treatment combination was used on triazine susceptible and triazine resistant plants. There were 3 replications. After spraying, the plants were placed in a 22C. leaf wetness chamber for 20 hours. They were then placed in growth cabinets set at 22C. day/16C. night with a 14 hour photoperiod. Observations were made 8 days after treatment (Table 10).

TABLE 10

Effect of atrazine and *Ascochyta* on triazine resistant and susceptible lamb's-quarters plants. (8 days after spraying)

| Treatments | Observations (of 3 replications) |
|---|---|
| 1. control (triazine-susceptible plants) | healthy |
| 2. control (triazine-resistant plants) | healthy |
| 3. *Ascochyta* (ChA 02W) alone (triazine-susceptible plants) | typical heavy *Ascochyta* infection on lower leaves |
| 4. *Ascochyta* (ChA 02W) alone (triazine-resistant plants) | typical heavy *Ascochyta* infection on lower leaves |
| 5. *Ascochyta* (ChA 02W) plus atrazine (triazine-resistant plants) | typical heavy *Ascochyta* infection on lower leaves |
| 6. atrazine (triazine-susceptible plants) | plants severely affected, leaves drying up |
| 7. atrazine (triazine-resistant plants) | healthy, leaves slightly mottled on one plant |

The observations indicate that Ascochyta causes disease on triazine resistant lamb's-quarters as well as triazine susceptible plants and that atrazine can be used in conjunction with Ascochyta.

EXAMPLE V

This example illustrates the host specificity of the pathogen, by spraying test species in the genus Chenopodium, economic species in the family Chenopodiaceae, and common unrelated crop species in which *Chenopodium album* can be found as a weed pest.

For each test, 3 plants were placed in a 12.5 cm pot. One pot of the test species was sprayed with the pathogen while a second pot containing the same species was sprayed with water. A lamb's-quarters plant was included to check for the efficacy of the inoculum. Test plants were sprayed with the pathogen at a rate of $10^8$ conidia/m$^2$. After spraying, all plants were subjected to a leaf wetness period of 20-24 hrs. After this period, the plants were placed in either a growth chamber or the greenhouse. One to 2 weeks after treatment, plants were checked and compared with their controls to determine if they were susceptible to the pathogen. Plant response to the pathogen was rated as susceptible (S), resistant (R) or immune (I).

Lamb's-quarters and most Chenopodium species are susceptible to *Ascochyta hyalospora* (Table 11). Of the Chenopodium species *C. ficifolium*, *C. hybridum*, *C. sandwicheum*, and *C. album* were the most susceptible. *C. ficifolium* was readily killed even at advanced stages of growth. Most cultivars of beets and spinach produced a hypersensitive response while all other plants tested were immune.

TABLE 11

Response of various plant species to *Ascochyta hyalospora* under controlled environment conditions

| Species tested | Disease Reaction |
|---|---|
| FAMILY CHENOPODIACEAE | |
| Genus Chenopodium | |
| *Chenopodium album* | S |
| *C. amaranticolor* | S |
| *C. bonus-henricus* | R |
| *C. botyrs* | R |
| *C. capitatum* | S |
| *C. ficifoium* | S |
| *C. foetidum* | S |
| *C. foliosum* | S |
| *C. glaucum* | R |
| *C. hybridum* | S |
| *C. murale* | S |
| *C. opulifolium* | S |
| *C. polysperum* | S |
| *C. polysperum-spicatum* | S |
| *C. quinoa* | S |
| *C. rubum* | R |
| *C. sandwicheum* | S |
| Related Economic Species | |
| Swiss Chard (*Beta vulgaris*) | |
| "Common Green" | I |
| "Silver Giant" | R |
| "Burgundy Crimson" | R |
| "Dorat" | I |
| Spinach (*Spinacia oleracea*) | |
| "America" | R |
| "Long Standing Bloomsdale" | R |
| "Tyee Hybrid" | R |
| "Hybrid Melodie" | R |
| Beet (*Beta vulgaris*) | |
| "Red Ace Hybrid" | R |
| "Garnet" | R |
| "Detroit Dark Red" | R |
| "Ruby Queen" | R |
| "Burpee's Golden" | R |
| "Tendersweet Cylindra" | R |
| "Early Wonder" | R |
| "Badger Baby" | R |
| "Lutz Green Leaf" | R |
| "Spinach Beet" | R |
| Sugar Beet (*Beta vulgaris*) | |
| "Klein Wanzleben" | I |
| Kochia | |
| "Childsii" | I |
| CROP PLANTS | |
| "Maple Arrow" Soybeans | I |
| "Early Sunglow" Sweetcorn | I |
| "Concorde" Spring Wheat | I |
| "Scott" Oats | I |

TABLE 11-continued

Response of various plant species to *Ascochyta hyalospora* under controlled environment conditions

| Species tested | Disease Reaction |
|---|---|
| "Green Arrow" Peas | I |

The embodiments of the invention in which an exclusive property or privilege is claimed are defined as follows:

1. A method for controlling growth of plants of Chenopodium weed species in agricultural crops which method comprises applying to the plants or to the locus of the plants an effective amount of the fungus *Ascochyta hyalospora* to effect and produce typical lesions in said plants so as to inhibit the growth of or kill said plants.

2. The method as claimed in claim 1, wherein the Chenopodium weed species is lamb's-quarter.

3. The method as claimed in claim 1, wherein the fungus is *Asochyta hyalospora* IMI 302770.

4. The method as claimed in claim 1 or claim 2, whereas the fungus is applied in the form of a foliar spray.

5. A method for controlling growth of lamb's-quarter plants in agricultural crops which method comprises applying to the plants or to the locus of the plants an effective amount of the fungus *Ascochyta hyalospora* IMI 302770 to effect and produce typical lesions in said plants so as to inhibit the growth of or kill said plants.

6. The method as claimed in claim 5, whereas the fungus is applied in the form of a foliar spray.

7. A plant growth regulating composition comprising an effective amount of a culture of microorganisms of the species *Ascochyta hyalospora* in association with an agriculturally acceptable carrier.

8. A composition as claimed in claim 7, wherein the fungus is *Ascochyta hyalospora* IMI 302770.

9. A biologically pure culture of the fungal microorganism having the identifying characteristics of *Ascochyta hyalospora* IMI 302770.

10. A plant growth regulating composition according to claim 7 wherein the composition also contains atrazine.

11. A method according to claim 1 wherein the *Ascochyta hyalospora* is associated with atrazine.

12. A method according to claim 5, wherein the *Ascochyta hyalospora* is associated with atrazine.

* * * * *